(12) United States Patent
Erpen

(10) Patent No.: US 12,295,586 B2
(45) Date of Patent: May 13, 2025

(54) DEVICE FOR CLOSING A VEIN JUNCTURE IN THE TREATMENT OF VARICOSE VEINS

(71) Applicant: Gefässpraxis Dr. Erpen AG, Visp (CH)

(72) Inventor: Thomas Erpen, Visp (CH)

(73) Assignee: GEFÄSSPRAXIS DR. ERPEN AG, Visp (CH)

( * ) Notice: Subject to any disclaimer, the term of this patent is extended or adjusted under 35 U.S.C. 154(b) by 353 days.

(21) Appl. No.: 17/308,770

(22) Filed: May 5, 2021

(65) Prior Publication Data

US 2021/0346034 A1    Nov. 11, 2021

(30) Foreign Application Priority Data

May 7, 2020 (EP) .................................... 20173475

(51) Int. Cl.
    *A61B 17/12*          (2006.01)
    *A61B 17/00*          (2006.01)
    (Continued)

(52) U.S. Cl.
CPC .. *A61B 17/12177* (2013.01); *A61B 17/00491* (2013.01); *A61B 17/12031* (2013.01);
(Continued)

(58) Field of Classification Search
CPC ........ A61B 17/12177; A61B 17/00491; A61B 17/12031; A61B 17/12109; A61B 17/12136; A61B 17/320725; A61B 2017/00778; A61B 2017/00951; A61B 2017/1205; A61B 2017/00004; A61B 2017/12081; A61B 17/12022; A61B 17/12122; A61B 17/12113;
(Continued)

(56) References Cited

U.S. PATENT DOCUMENTS 5,562,728 A * 10/1996 Lazarus ................. A61B 17/11
                                                   623/1.34
5,634,901 A * 6/1997 Alba ...................... A61F 2/958
                                                   604/96.01
(Continued)

FOREIGN PATENT DOCUMENTS

CN    113274099 A * 8/2021 ......... A61B 17/3207
EP    3 135 206      1/2020
(Continued)

OTHER PUBLICATIONS

European Search Report for 20 17 3475 dated Nov. 2, 2020, 5 pages.

*Primary Examiner* — Jocelin C Tanner
(74) *Attorney, Agent, or Firm* — NIXON & VANDERHYE

(57) ABSTRACT

The invention relates to a device for closing a vein juncture in the treatment of varicose veins including a catheter which can be inserted into a venous system and at the distal end of which an expandable balloon is arranged, a covering which is arranged circumferentially on the balloon and can be expanded by means of said balloon, wherein the proximal covering end is designed to be open, and at least one adhesion agent for acting on the expanded covering such that it adheres to a vein wall in order to close the vein juncture.

19 Claims, 8 Drawing Sheets

(51) Int. Cl.
*A61B 17/3207* (2006.01)
*A61L 31/00* (2006.01)
*A61M 25/10* (2013.01)

(52) U.S. Cl.
CPC .. *A61B 17/12109* (2013.01); *A61B 17/12136* (2013.01); *A61B 17/320725* (2013.01); *A61L 31/005* (2013.01); *A61B 2017/00778* (2013.01); *A61B 2017/00951* (2013.01); *A61B 2017/1205* (2013.01); *A61M 2025/1056* (2013.01)

(58) Field of Classification Search
CPC ........ A61B 17/12099; A61B 17/12168; A61B 17/0057; A61B 2017/00575; A61B 2017/00597; A61B 2017/00615; A61B 2017/00632; A61B 17/12118; A61B 17/12027; A61B 2017/12054; A61L 31/005; A61M 2025/1056; A61F 2/86; A61F 2/958; A61F 2/0105
USPC ........................................................ 606/159
See application file for complete search history.

(56) References Cited

U.S. PATENT DOCUMENTS

| | | | |
|---|---|---|---|
| 6,379,329 B1* | 4/2002 | Naglreiter | A61B 17/12136 604/101.02 |
| 6,638,293 B1 | 10/2003 | Makower et al. | |
| 10,300,250 B2 | 5/2019 | Erpen | |
| 2002/0002401 A1 | 1/2002 | McGuckin, Jr. et al. | |
| 2002/0049492 A1* | 4/2002 | Lashinski | A61F 2/86 623/1.36 |
| 2003/0073979 A1 | 4/2003 | Naimark et al. | |
| 2004/0098030 A1 | 5/2004 | Makower et al. | |
| 2004/0186561 A1 | 9/2004 | McGuckin, Jr. et al. | |
| 2005/0107867 A1* | 5/2005 | Taheri | A61B 17/12022 623/1.38 |
| 2005/0177106 A1 | 8/2005 | Naimark et al. | |
| 2006/0190076 A1 | 8/2006 | Taheri | |
| 2006/0206140 A1* | 9/2006 | Shaolian | A61B 17/12022 606/200 |
| 2006/0282158 A1 | 12/2006 | Taheri | |
| 2006/0282159 A1 | 12/2006 | Taheri | |
| 2006/0292206 A1 | 12/2006 | Kim et al. | |
| 2007/0050008 A1 | 3/2007 | Kim et al. | |
| 2007/0055355 A1 | 3/2007 | Kim et al. | |
| 2007/0061005 A1 | 3/2007 | Kim et al. | |
| 2008/0045996 A1 | 2/2008 | Makower et al. | |
| 2009/0112239 A1* | 4/2009 | To | A61M 25/104 604/103.05 |
| 2009/0131882 A1 | 5/2009 | Naimark et al. | |
| 2011/0208221 A1* | 8/2011 | Gennrich | A61F 2/90 606/159 |
| 2012/0232581 A1* | 9/2012 | Schonholz | A61B 17/0057 606/213 |
| 2012/0323270 A1* | 12/2012 | Lee | A61B 17/1219 606/213 |
| 2012/0330343 A1 | 12/2012 | Kim et al. | |
| 2013/0261724 A1 | 10/2013 | Kim et al. | |
| 2014/0081374 A1 | 3/2014 | Kim et al. | |
| 2014/0142685 A1 | 5/2014 | Kim et al. | |
| 2014/0180069 A1* | 6/2014 | Millett | A61B 8/12 600/463 |
| 2014/0207226 A1 | 7/2014 | Kim et al. | |
| 2016/0113659 A1 | 4/2016 | Kim et al. | |
| 2016/0135945 A1 | 5/2016 | Kim et al. | |
| 2016/0242790 A1* | 8/2016 | Brandeis | A61B 17/320725 |
| 2017/0020653 A1 | 1/2017 | Kim et al. | |
| 2017/0056048 A1* | 3/2017 | Erpen | A61B 17/320725 |
| 2020/0022801 A1 | 1/2020 | Kim et al. | |
| 2020/0022802 A1 | 1/2020 | Kim et al. | |

FOREIGN PATENT DOCUMENTS

| | | | |
|---|---|---|---|
| WO | 97/27893 | 8/1997 | |
| WO | 02/03893 | 1/2002 | |
| WO | 03/032815 | 4/2003 | |
| WO | 2004/045393 | 6/2004 | |
| WO | 2005/048884 | 6/2005 | |
| WO | 2014/201434 | 12/2014 | |
| WO | 2015/052703 | 4/2015 | |
| WO | WO-2019075354 A1 * | 4/2019 | ....... A61B 17/12031 |

* cited by examiner

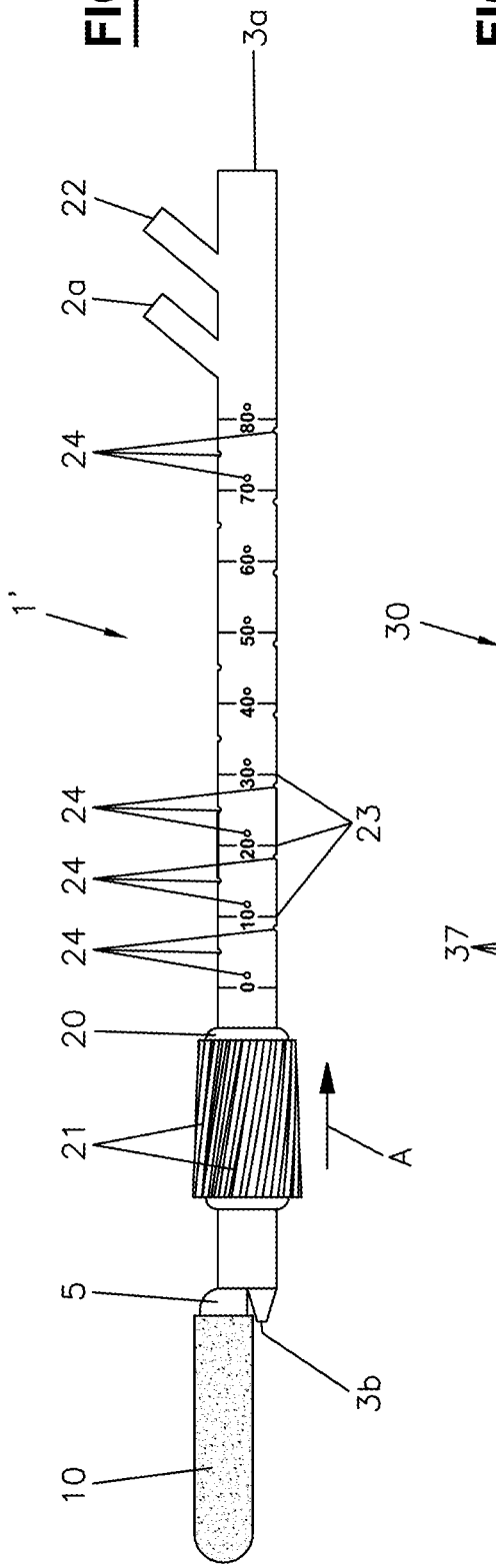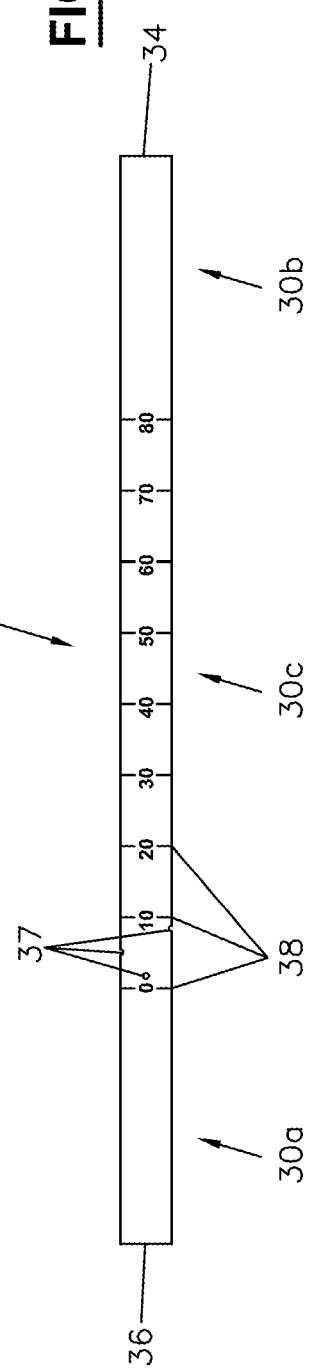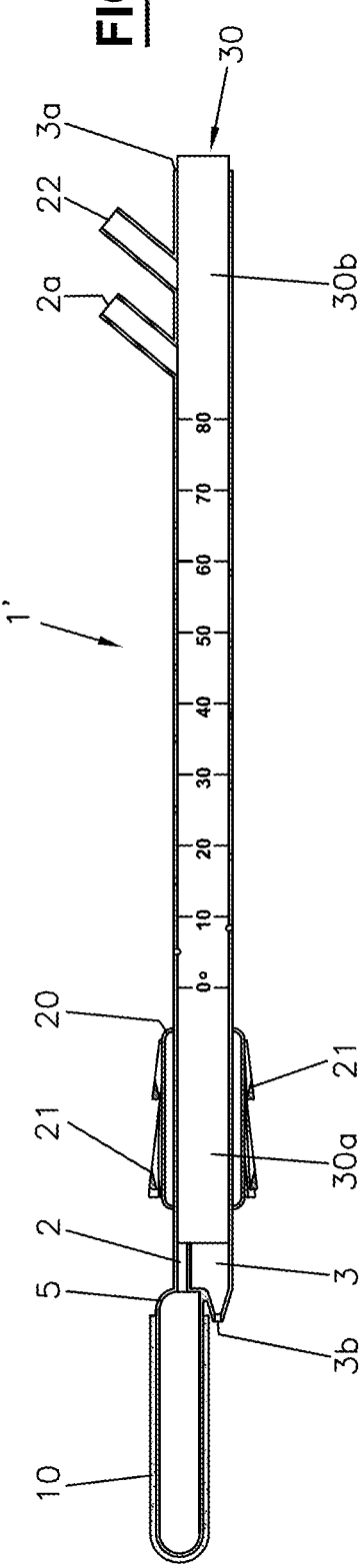

DEVICE FOR CLOSING A VEIN JUNCTURE IN THE TREATMENT OF VARICOSE VEINS

CROSS-REFERENCE TO RELATED APPLICATIONS

This application claims foreign priority to foreign application EP 20173475, filed May 7, 2020 in the European Patent Office, the entire contents of which is hereby incorporated by reference.

FIELD OF THE INVENTION

The invention relates to a device for closing a vein juncture in the treatment of varicose veins.

BACKGROUND OF THE INVENTION

Newer endovenous methods for the treatment of varicose veins are known, in which laser, radio frequency or glue are used for bonding. These procedures are problematic when treating the vena saphena *magna* or the vena saphena *parva* because the cross ("saphenofemoral junction" or "saphenopopliteal junction") cannot be closed with precision. If the treatment leads too closely to the cross, there is a risk of thrombosis and embolism. If the treatment is too far from the cross, a relapse can occur.

In varicose veins, the perforating veins can also be affected, in which the physiological flow direction is directed from the superficial veins into the deep veins. In the case of insufficiency of the perforating veins, the flow reverses in the perforating veins with stases of the superficial veins. The endovenous procedures mentioned above do not offer an optimal solution for also treating the problem of insufficient perforating veins.

SUMMARY OF THE INVENTION

The problem addressed by the present invention is that of providing a device which allows for a safe closing of a vein juncture in the treatment of varicose veins.

A device which solves this problem comprises a catheter which can be inserted into a venous system, an expandable balloon which is arranged at a distal end of the catheter, a covering which is arranged circumferentially on the balloon and can be expanded by means of the balloon, and at least one adhesion agent for acting on the expanded covering such that it adheres to a vein wall in order to close the vein juncture. The covering extends from a proximal covering end which is designed to be open to a distal covering end.

The device can be designed for different applications. In one application, the cross of the vena saphena *magna/parva* can be sealed with millimeter precision, so that no thrombosis can penetrate the deep leg venous system and there is no risk of early variceal recurrence.

In another application, a perforating vein can be safely sealed, so that the reflux in the region of the perforating vein can be corrected without endangering the deep leg venous system.

The device can be configured in different ways. For example, the covering of the device can have a tubular central part which is designed to be open either only at one covering end or at both covering ends. The covering is designed, e.g., like a sack, so that, in the expanded state, it can be used to delimit a free space in the vein, which is closed at one end and open at the other end. In another embodiment, the covering is designed to be continuously tubular, so that, in the expanded state, it can be used to delimit a free space in the vein, which is open at both ends.

BRIEF DESCRIPTION OF DRAWINGS

Further specific design features of the device and their advantages are apparent from the following description and drawings of embodiments, in which:

FIG. 17 is a side view of another further variant of the device without an inner catheter;

FIG. 18 is a side view of the inner catheter for the device according to FIG. 17;

FIG. 19 is a partially sectional side view of the device according to FIG. 17 with an inserted inner catheter according to FIG. 18;

DETAILED DESCRIPTION OF THE PREFERRED EMBODIMENTS

In the following description, the terms "proximal" and "distal" are used from the perspective of the user of the device. The proximal end is thus the end facing the user and the distal end is the end facing away from the user.

First Embodiment

Figure 1:
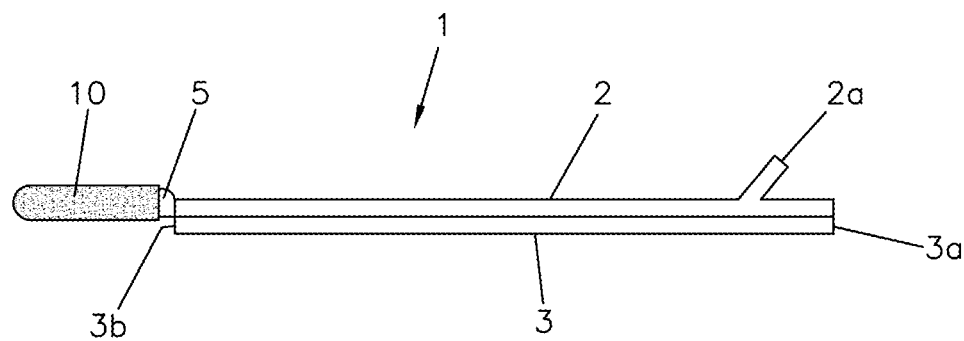
FIG. 1 is a side view of a first embodiment of a device.

FIG. 1 shows a catheter 1 which can be inserted into a vein and which has an expandable balloon 5 at the distal end. An expandable covering 10 is arranged on said balloon. The catheter 1 has a first channel 2 which fluidically connects a connection 2a to the balloon 5, and a second channel 3 which connects an inlet opening 3a to an outlet opening 3b.

For example, a syringe or the like can be connected to the connection 2a in order to pump a fluid into, or remove said fluid from, the balloon 5 via the first channel 2 and thus enable the balloon 5 to inflate and deflate. In order to not endanger a patient by a possible leakage of the balloon 5 inserted into the vein, a liquid, for example, a sodium chloride solution, instead of air is used as the fluid for inflating.

Figure 2:
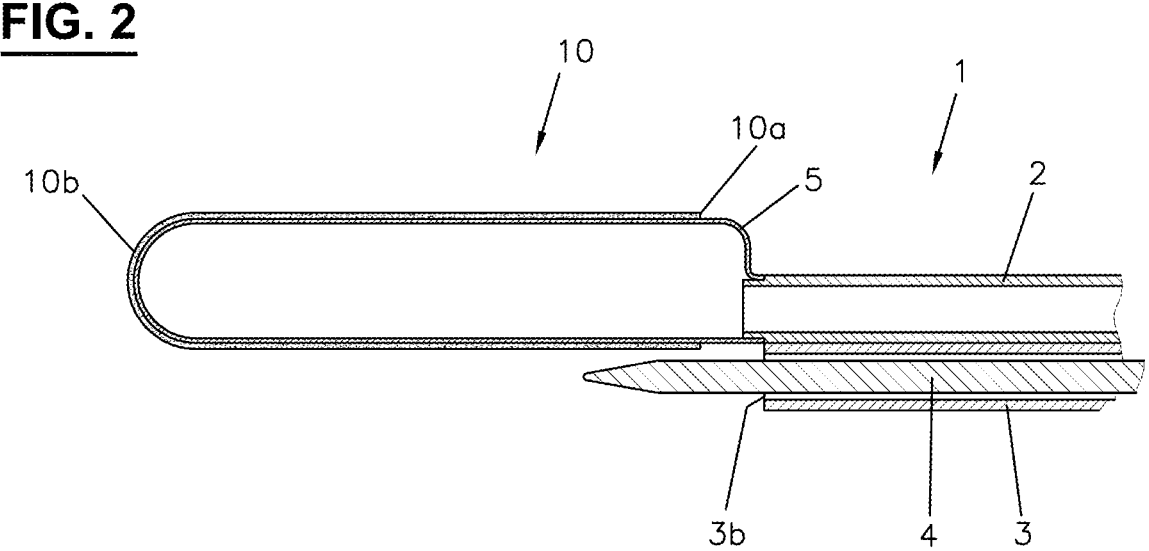
FIG. 2 is a sectional side view of the front part of the device according to FIG. 1 together with a guide wire.

As FIG. 2 shows, a guide wire 4 can be accommodated in the second channel 3. In the non-expanded state, the balloon 5 and the covering 10 are arranged in relation to the outlet opening 3b such that there is sufficient space on the side for the guide wire 4 to be guided past them.

The covering 10 is shaped like a sack and is therefore designed to be open at the proximal covering end 10a and closed at the distal covering end 10b. The length of the covering 10 (distance between the ends 10a and 10b) is typically less than 10 cm in the non-expanded state.

The covering 10 is designed as a thin layer similar to a membrane and is impermeable to blood, in particular the blood plasma.

The covering 10 consists of a material that is tolerated by the body, e.g., bovine pericardium. Another biological or synthetic material that is tolerated and not rejected by the body can also be used. The material of the covering 10, which is intended to remain in the body at least for a time, is soft, so that it does not hurt and/or chafe during movements, in particular movements of the hip joint, when the covering 10 is used in its vicinity.

Depending on the intended use, the material of the covering 10 is selected such that it is not broken down by the body or dissolves after a certain time. In the latter case, the period of time until resorption is at least long enough to prevent the forming of a neo-cross when the device is used to close the cross.

The device described herein can be used in many ways to close a vein juncture.

Figure 3:
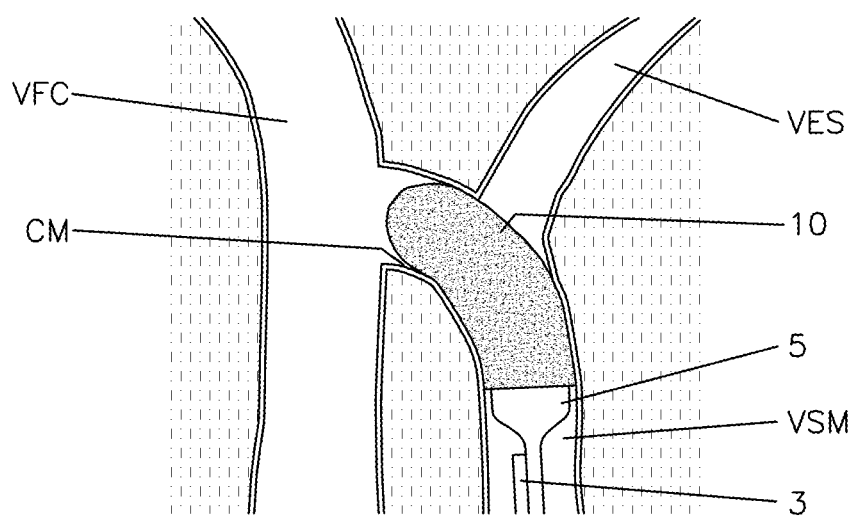
FIG. 3 is a schematic view of the veins in the region of the cross of the vena saphena *magna* with the inserted device according to FIG. 1.

FIG. 3 shows, e.g., the juncture CM of the vena saphena *magna* VSM and the vena *femoralis communis* VFC ("cross"). The vena epigastrica superficialis VES is also shown, which opens into the vena saphena *magna* VSM.

During use, the guide wire 4 is pushed into the vein VSM to the cross CM and the device according to FIG. 1 subsequently is inserted into the vein VSM by sliding the second channel 3 over the wire 4. If the balloon 5 together with the covering 10 is at the desired location, the guide wire 4 is removed. Then the balloon 5 is inflated. The covering 10 expands accordingly, cf. FIG. 3. The covering 10 eventually comes into contact with the vein wall and adheres to it. The balloon 10 is emptied and removed from the vein VSM. The covering 10 is now in place, as shown in FIG. 4.

The cross CM is now closed and the vein VSM can be treated further, e.g., as described below in connection with FIG. 17-19.

Figure 4:
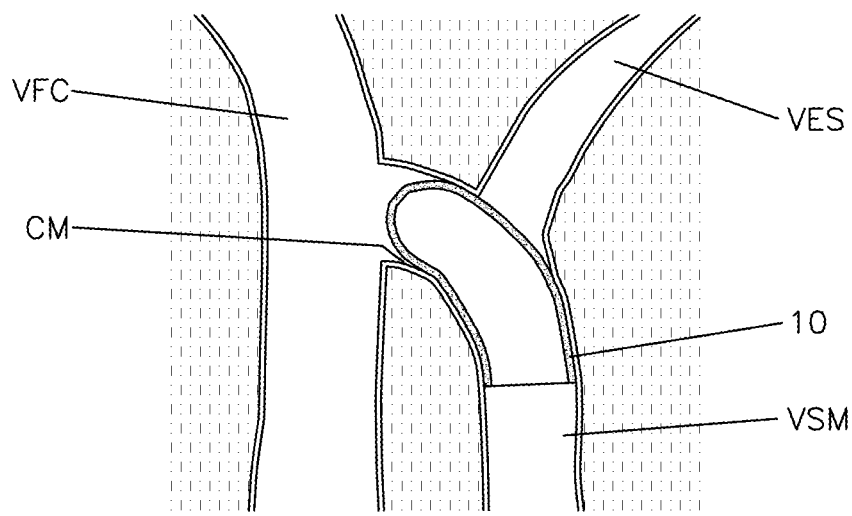
FIG. 4 is the view according to FIG. 3 after the treatment, wherein the covering is shown in section.
Figure 5:
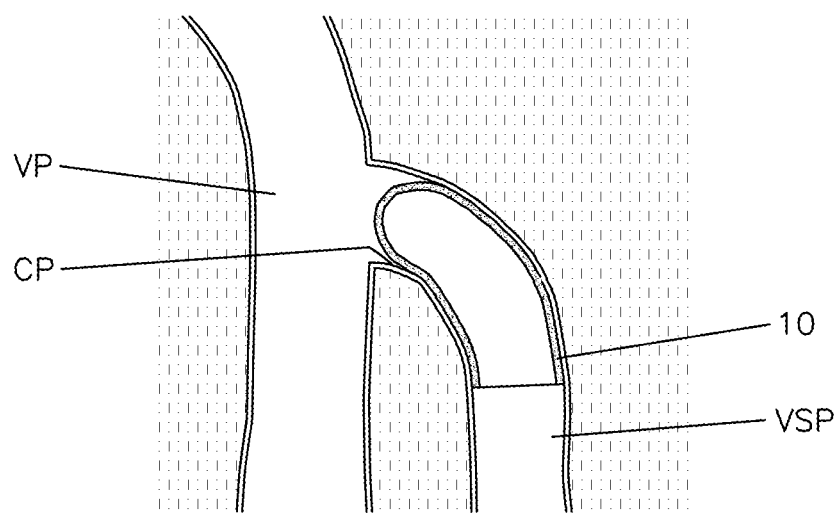
FIG. 5 is a schematic view of the veins in the region of the cross of the vena saphena *parva* after the treatment, wherein the covering is shown in section.

FIG. 5 shows another example in which the covering 10 has been placed in a manner analogous to the example according to FIG. 4 such that the cross CP of the vena saphena *parva* VSP, which opens into the vena poplitea VP, is closed.

The covering 10 can be made to adhere to the vein wall by means of at least one adhesion agent. Said adhesion agent is designed such that, together with the covering 10, a non-rigid structure is created which allows for painless movements.

An adhesion agent can be provided in a variety of ways:

The covering 10 can have, e.g., an outer layer which adheres to the vein wall when it comes into contact with said vein wall. The outer layer is preferably expandable and can contain collagen, for example.

Figure 6:
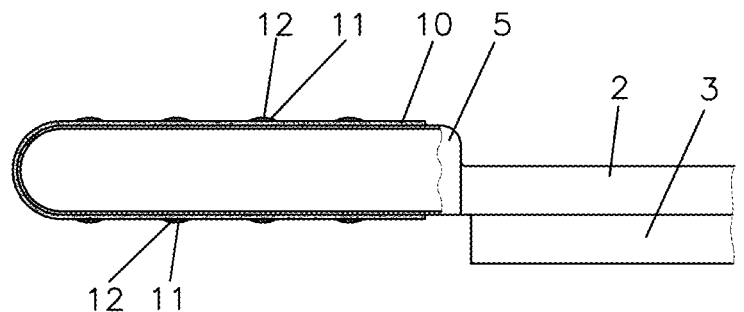
FIG. 6 is a partially sectional side view of the front part of a variant of the device.
Figure 7:
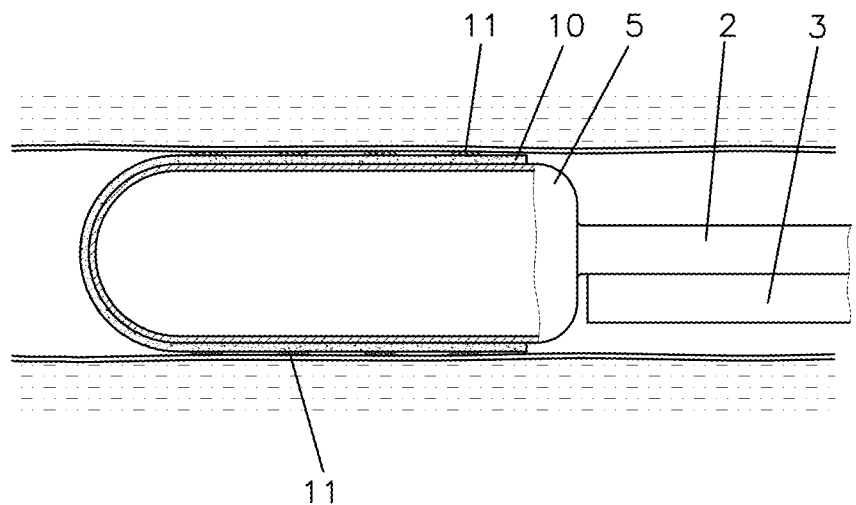
FIG. 7 shows the device according to FIG. 6 in a vein, wherein the balloon and the covering are in the expanded state.

FIG. 6 shows an example in which the covering 10 circumferentially has a plurality of reservoirs on its surface, which contain a body-compatible adhesive 11 and are covered by a membrane 12. When the balloon 5 is inflated, the membranes 12 burst and the adhesive 11 is released. If the balloon 5 is sufficiently expanded, as shown in FIG. 7, the adhesive 11 comes into contact with the vein wall, so that the covering 10 is adhered to it. A tissue adhesive based, e.g., on cyanoacrylate, is suitable as the adhesive 11.

Figure 8:
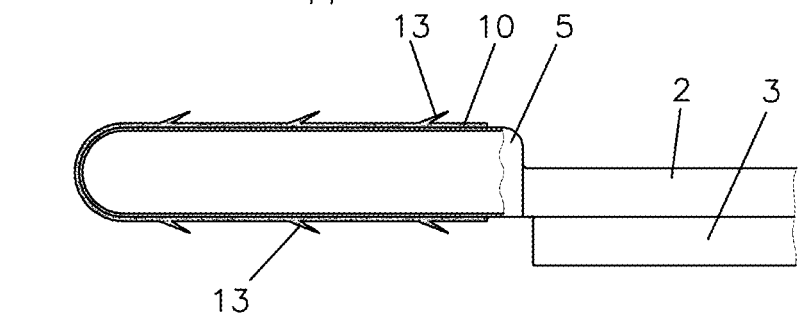
FIG. 8 is a partially sectional side view of the front part of a further variant of the device.
Figure 9:
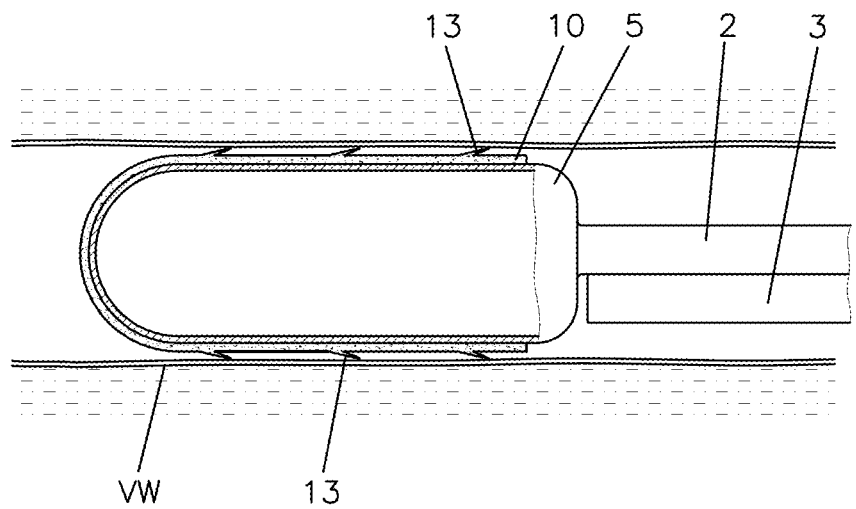
FIG. 9 shows the device according to FIG. 9 in a vein, wherein the balloon and the covering are in an expanded state.
Figure 10:
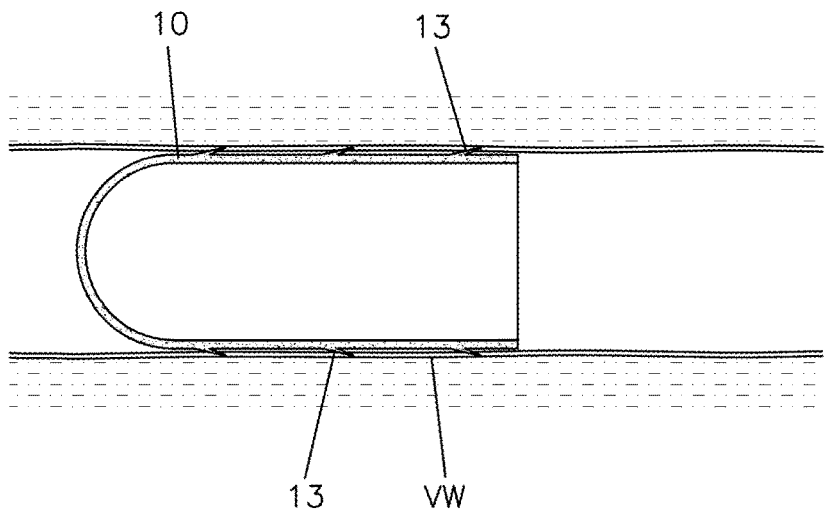
FIG. 10 is the view according to FIG. 9 after the treatment.

FIG. 8 shows an example in which the covering 10 is provided on the outer side and circumferentially with hook elements 13 which are designed to engage in the vein wall. When the balloon 9 is expanded, cf. FIG. 9, the hook elements 13 come into contact with the vein wall VW and are subsequently anchored therein, cf. FIG. 10.

Figure 11:
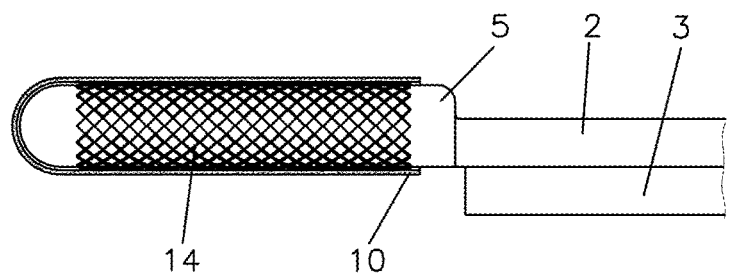
FIG. 11 is a side view of the front part of another further variant of the device, wherein the covering is shown in section.

FIG. 11 shows an example in which the covering 10 is provided with a tubular lattice structure 14. This can be designed, e.g., similarly to a stent but in this case does not necessarily extend over the entire length of the covering 10. The lattice structure 14 expands when the balloon 5 is expanded and remains in the expanded state when the balloon 5 is removed. In this case, the lattice structure 14 is arranged between the balloon 5 and the covering 10. It can also be arranged on the outer side of the covering 10. The lattice structure 14 can be attached to the covering 14. The lattice structure 14 is made of a body-compatible material, e.g., metal. Depending on the intended use, the material is absorbable.

Figure 12:
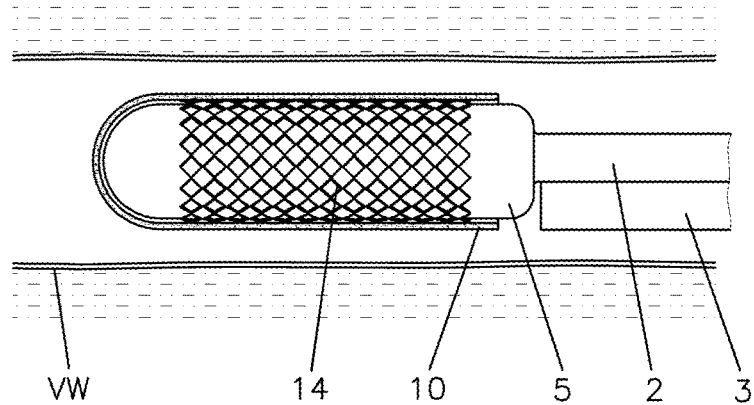
FIG. 12 shows the device according to FIG. 11 in a somewhat expanded state in a vein.
Figure 13:
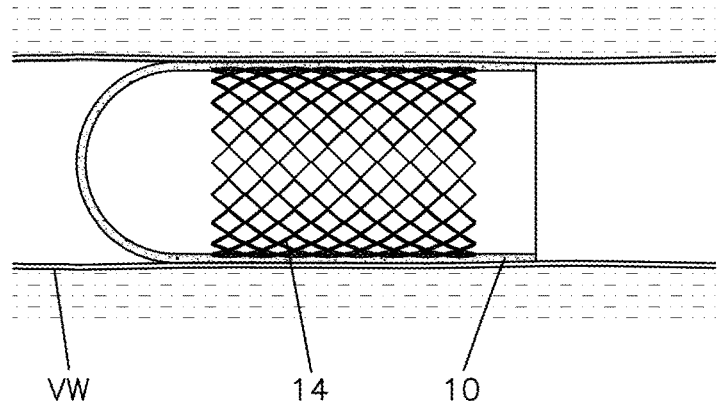
FIG. 13 is the view according to FIG. 12 after the treatment.

During use, the balloon 5 together with the elements 10 and 14 arranged thereon is brought to the desired location in the vein and then inflated, cf. FIG. 12, until the covering 10 bears against the vein wall VW. The balloon 5 is emptied and taken out. The covering 10 is securely fastened on the vein wall VW by means of the lattice structure 14, cf. FIG. 13.

Figure 14:
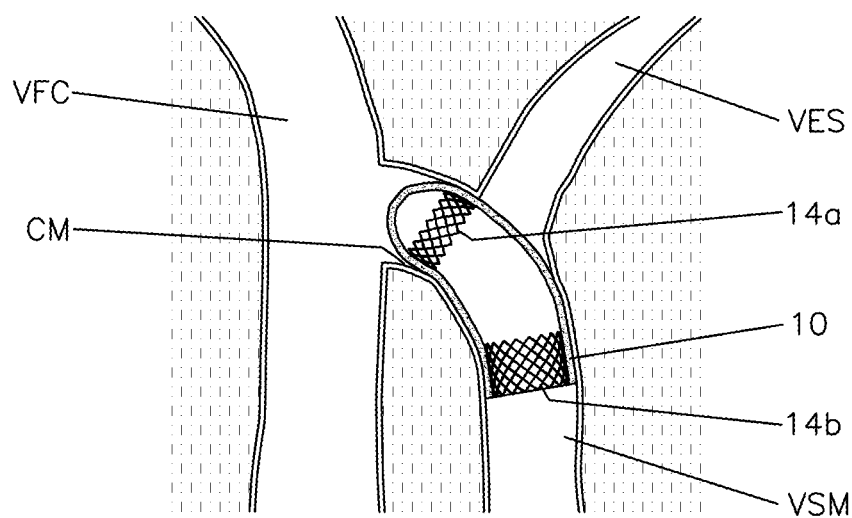
FIG. 14 is a schematic view of the veins in the region of the cross of the vena saphena *magna*, in which a covering with lattice structures has been placed, wherein the covering is shown in section.

As an alternative to the embodiment according to FIG. 11, it is also conceivable to provide two or more lattice structures which are arranged along the balloon 5. For example, it is conceivable to provide two lattice structures which are each arranged at the ends of the covering 10, so that a portion is created in between them which is only formed by the covering 10. FIG. 14 shows an example of a covering 10 with two lattice structures 14 a, 14b, which has been placed in the cross CM. The respective lattice structure 14a, 14b is arranged on the covering 10, i.e., on or in the covering 10, and is preferably attached thereto.

Figure 15:
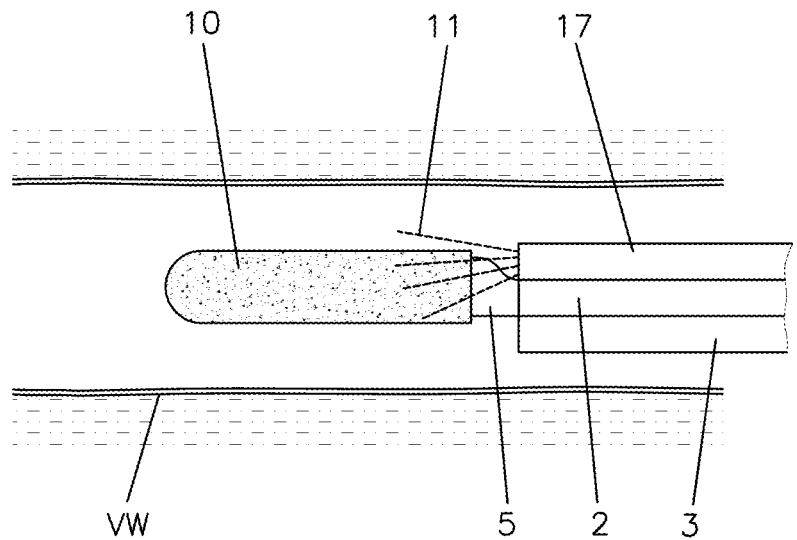
FIG. 15 shows the front part of a further variant of the device in a vein.
Figure 16:
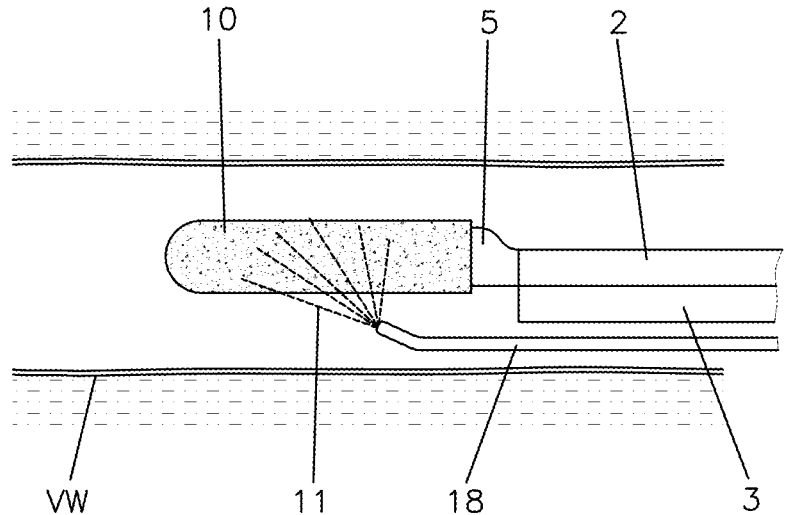
FIG. 16 shows the front part of another further variant of the device in a vein.

FIGS. 15 and 16 show variants in which an adhesive 11 can be applied within the vein to the surface of the covering 10 after the balloon 5 has been placed but not yet expanded. The adhesive 11 is dispensed and spreads over the covering 10. The balloon 5 is subsequently inflated and the covering 10 is thus glued to the vein wall VW.

In the variant according to FIG. 15, at least one further channel 17 is attached to the catheter 2, 3 and fluidically connected to a further connection at the proximal end of the catheter 2, 3 for introducing the adhesive 11.

In the variant according to FIG. 16, the further channel 18 is formed separately from the catheter 2, 3. The further channel 18 is inserted, e.g., by means of a second venipuncture.

FIG. 17-19 show a supplemented embodiment in which the device, in addition to the closure of a vein juncture, allows for a treatment of the vein by applying a sclerosant and by cutting. This treatment is described in U.S. Pat. No. 10,300,250B2 by the same applicant.

The catheter 1' is an outer catheter and has the balloon 5 with the expandable covering 10 at the distal end. As FIG. 19 shows, the balloon 5 is fluidically connected via a first channel 2 to the connection 2a at the proximal end. The catheter 1' has the second channel 3 which connects the inlet opening 3a to the outlet opening 3b and in which a guide wire can be accommodated.

Following balloon 5, a further balloon 20 with cutting elements 21 is arranged on the catheter 1'. The further balloon 20 is fluidically connected to a further connection 22 at the proximal end of the catheter 1' via a further channel (not depicted herein). As in the case of balloon 5 and the connection 2a, a fluid can be pumped into the balloon 20 via the connection 22 in order to inflate it.

The catheter 1' is fenestrated. For this purpose, it is provided with side openings 24 ("catheter windows") between the balloon 20 and the connections 2a, 22. Said side openings are arranged to be distributed around the circumference of the catheter 1' and are fluidically connected to the inlet opening 3a via the channel 3. During use, a sclerosant can be injected into the vein to be treated via the side openings 24. Two adjacent side openings 24 are arranged axially and radially offset to one another. The offset allows for a most homogeneous distribution of sclerosant in the vein.

Markings 23 are provided on the catheter shaft between the balloon 20 and the connections 2a, 22, which are attached, for example, at regular intervals and, among other things, provide information about how far the catheter 1' has been inserted into a vein. In the variant according to FIG. 17, markings 23 in the form of lines and numbers 0, 10, 20, 30, ..., 80 can be seen. Of course, other types of markings are also possible.

The side openings 24 are arranged in groups, so that the part of the catheter 1' provided with the side openings 24 is divided into portions which each have the same arrangement of side openings 24. In the example according to FIG. 17, e.g., a group with three side openings can be seen between the portion 0 to 10. The same arrangement of side openings is repeated in the respective subsequent section 10 to 20, 20 to 30, etc.

The side openings 24 in the respective group are arranged radially offset by an angle. In the example with three side openings, this angle can be 120 degrees. However, an uneven radial distribution is also conceivable. Furthermore, the number of side openings 24 per group or portion can be different from the one shown in FIG. 17 and can be one, two or more. Since the side openings 24 extend through the outer wall of the catheter 1', the number and arrangement are selected such that there is enough space to be able to provide the channels from the connections 2a and 22 to the balloons 5 and 20.

A second catheter 30 (hereinafter also called "inner catheter"), as shown in FIG. 18, can be inserted via the inlet opening 3a of the catheter 1'. The catheter 30 has a distal end portion 30a and a proximal end portion 30b with a connection 34. The distal end portion 30a is formed by a closed wall. In particular, in contrast to the end opening 3b in the outer catheter 1', the end 36 of the end portion 30a is free of an end opening. The closed end 36 of the inner catheter 30 allows the lumen at the tip of the outer catheter 1' to be closed, which prevents sclerosant from flowing out through the outlet opening 3b.

Between the two end portions 30a and 30b, the catheter 30 has an intermediate part 30c which has an inner channel ("lumen") and which is provided with side openings 37. They are fluidically connected to the connection 34 via the inner channel. Adjoining the distal closed end portion 30a, the catheter 30 is provided with side openings 37 only on a partial portion, while the rest of the catheter shaft has no openings. In contrast to the outer catheter 1', only a single group of side openings 37 is therefore provided. The number and/or arrangement of the side openings 37 preferably corresponds to the number or arrangement of the first group of side openings 24 in the outer catheter 1'. In the example according to FIG. 18, three side openings 37 can be seen which are arranged radially and axially offset to one another similar to the side openings 24 in a group in the outer catheter 1' according to FIG. 17. Depending on the design, the number of side openings 37 can be one, two or more.

Markings 38 are provided along the intermediate part 30c of the catheter 30, which are attached, for example, at regular intervals and, among other things, provide information about how far the catheter 30 is inserted into the outer catheter 1'. For example, lines, numbers, etc. serve as markings 38.

The outer shape of the inner catheter 30 is designed such that space can be provided in the outer catheter 1' for the channel 2 to balloon 5 and for the channel to balloon 20.

During use, the inner catheter 30 is accommodated in the outer catheter 1' and then retracted in portions. In this case, the side openings 38 are first located in the vicinity of the side openings 24 of the first group, then at the side openings 24 of the second group, etc., and the closed end portion 30a of the inner catheter 30 seals the channel 3 of the outer catheter 1' between the ends 3b and 36. A sclerosant can thus be introduced in sections into the vein to be treated via the connection 34 and the side openings 37 and 24.

In FIGS. 17 and 19, the balloon 20 is shown in a slightly inflated state. In the following, "axial" refers to the direction in which the axis A runs, along which the outer catheter 1' extends from the outlet opening 3b to the inlet opening 3a, while "radial" refers to the direction transverse to axis A.

The balloon 20 is a "cutting balloon" and for this purpose has one or more cutting elements 21 ("blades"). A respective cutting element 21 does not run in a straight line as seen looking in the axial direction A.

Various forms of courses for the cutting element 21 are conceivable. For example, the cutting edge of a cutting element can be curved such that it winds around the axis A, e.g., in a helical manner. It is also conceivable that, as seen looking in the direction of the axis A, the cutting edge has a portion with a straight axial path which merges into another straight portion via a curved intermediate portion. It is also conceivable to provide only a single cutting element 3 which runs around the axis A.

The overall non-straight path of a cutting element 3 has the effect that, as seen looking in the axial direction A, the ends of a cutting element 3 are arranged radially offset by an angle which is greater than 0 degrees. The angle is preferably at least 10 degrees and particularly preferably at least 20 degrees. Furthermore, the path can be such that said angle is less than 360 degrees. It is preferably at most 180 degrees and particularly preferably at most 90 degrees.

The maximum extension of a cutting element 21 perpendicular to the axis A can also be variable in that the cutting edge runs at a height which decreases in the direction of the connection 3a. In the present embodiment, the cutting element 21 is designed to be wedge-shaped. The maximum height H of a cutting element 21 is typically in the range of 0.5-1.5 mm.

The balloon 21 extends axially over a length which is typically in the range of 5-30 mm.

The axially and/or radially variable shaping of a cutting element 21 allows for a comprehensive mechanical effect on an inner wall of the vein when the catheter 1' inserted into the vein is retracted again. The tapering cutting edges of the cutting elements 21 gradually dig into the inner wall of the veins, similar to a plow. An abrupt mechanical action is therefore avoided, so that a more painless treatment is possible which under certain circumstances can also be carried out without local anesthesia in the form of a tumescence anesthesia. This is the case, e.g., when Aethoxysklerol® is used as a sclerosant, which is also a local anesthetic.

The device according to FIG. 17-19 can be used, e.g., as follows:

The catheter 1' is inserted into the saphenous vein VSM, possibly by means of a guide wire, and the covering 10 is placed by inflating and deflating the balloon 5, so that the cross CM is closed, cf. FIG. 4.

The balloon 20 is subsequently inflated. The inner catheter 30 is inserted into the channel 3 of the outer catheter 1', unless it has already been inserted together with the catheter 1' in the event that no guide wire has been used.

The sclerosant is introduced via the inner catheter 30 by means of a syringe attached to the connection 34. The inner catheter 30 is retracted, e.g., in 10 cm steps. Sclerosant is applied every 10 cm and after a specific waiting period, e.g., approximately 1 minute, the next portion is treated. The procedure is continued until the entire inner catheter 30 is removed.

The effect to the sclerosant has resulted in vasospasm. In addition, the sensitivity to pain should also be reduced. The catheter 1 with the inflated balloon 20 is now slowly retracted. Due to the mechanical effect of a cutting element 21 on the balloon 20, the intima and media of the vein are destroyed. The special shaping of a cutting element 21 allows for an effective destruction of the inner wall of the vein which is cut into multiple fragments when the balloon 20 is retracted.

Second Embodiment

Figure 20:
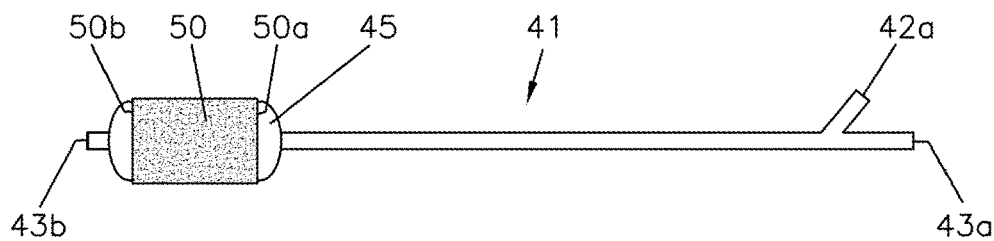
FIG. 20 is a side view of a second embodiment of a device.

In the embodiment shown in FIG. 20, the device comprises a catheter 41 having a first channel which connects an inlet opening 43a to the outlet opening 43b and which is designed to accommodate a guide wire 4 (cf. FIG. 2). A balloon 45 is arranged at the distal end of the catheter 41. Said balloon runs around the outer wall of the catheter 41, so that the first channel can extend through the balloon 45 and the outlet opening 43b is axially offset from the balloon 45. The balloon 45 is fluidically connected via a second channel to a connection 42a at the proximal end of the catheter 41. A fluid can be conveyed via the second channel in order to be able to inflate and deflate the balloon 45.

An expandable covering 50 is arranged on the balloon 45. Similarly to the covering 10 in the first embodiment, it is designed as a membrane and can consist of the same material.

In contrast to the covering 10, the covering 50 is open on both covering ends 50a, 50b and is thus of a continuous tubular design.

In the unexpanded state, the length of the covering 50 (the distance between the ends 50a and 50b) is typically less than 10 cm. The covering on the balloon has a maximum width of at most 2 cm in the expanded state. The maximum width is preferably in the range of 0.5-1.5 cm.

For securing the covering 50 to a vein wall, at least one adhesion agent is provided which can be designed as in the first embodiment: Providing an adhering outer layer on the covering 50; providing adhesive 12 by means of reservoir 11 and/or through a further channel 17, 18; providing hook elements 13; providing one or more expandable lattice structures 14; etc.

The device according to FIG. 20 can be used, e.g., to close a vein juncture into a perforating vein.

Figure 21:
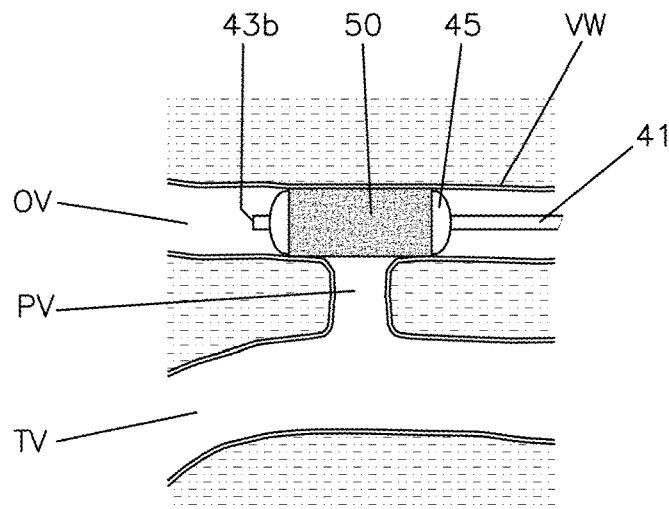
FIG. 21 is a schematic view of the veins in the region of a perforating vein with an inserted device according to FIG. 20.
Figure 22:
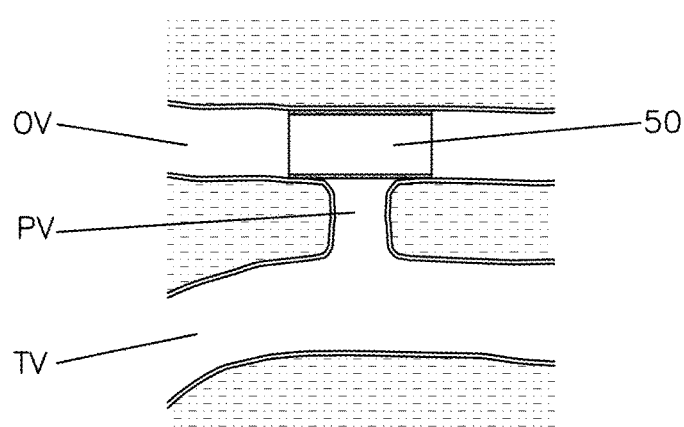
FIG. 22 is the view according to FIG. 21 after the treatment, wherein the covering is shown in section.

FIG. 21 schematically shows a perforating vein PV which connects a superficial vein OV with a deep vein TV. The perforating vein PV is insufficient and is supposed to be closed down. The procedure for this purpose is as follows:

After the guide wire 4 has been pushed under ultrasound control via the vein OV into the region of the perforating vein PV to be treated, the catheter 41 is advanced along the guide wire 4 until the balloon 45 together with the covering 50 covers the perforating vein PV. The guide wire 4 is removed and the balloon 45 is inflated until the covering 50 contacts the vein wall VW, cf. FIG. 21. Due to the adhesion agent, the covering 50 remains adhered to the vein wall VW. The balloon 45 is emptied and removed by pulling out the catheter 41. The vein juncture into the perforating vein PV is now closed by means of the covering 50, cf. FIG. 22.

Figure 23:
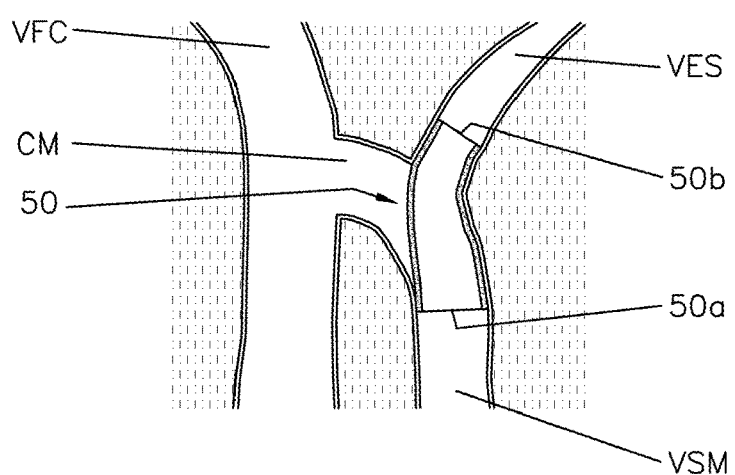
FIG. 23 is a schematic view of the veins in the region of the cross of the vena saphena *magna* after the treatment with the device according to FIG. 20, wherein the covering is shown in section.

The device according to FIG. 20 can also be used for the treatment of the *magna* cross CM. FIG. 23 shows the situation in which the covering 50, which is open on both sides, has been placed such that the open end 50b extends into the vena epigastrica superficialis VES, thus sealing the connection to the vena *femoralis communis* VFC.

Figure 25:
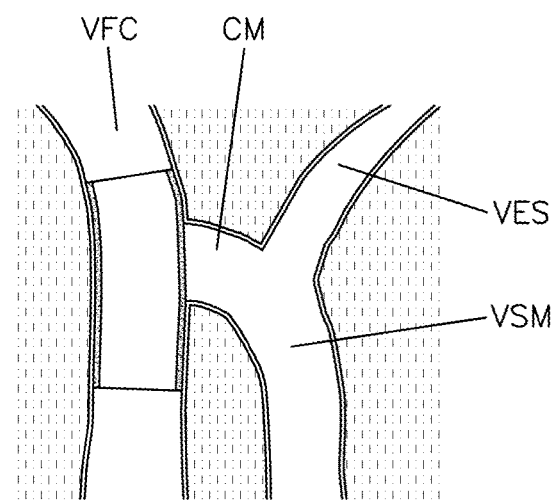
FIG. 25 is a schematic view of the veins in the region of the cross of the vena saphena *magna* after the treatment with the device according to FIG. 20, wherein the covering is shown in section.

As a further application variant, it is possible to place the covering 50 such that it closes the vena saphena *magna* VSM or its cross CM from the vena *femoralis communis* VFC, cf. FIG. 25.

Figure 24:
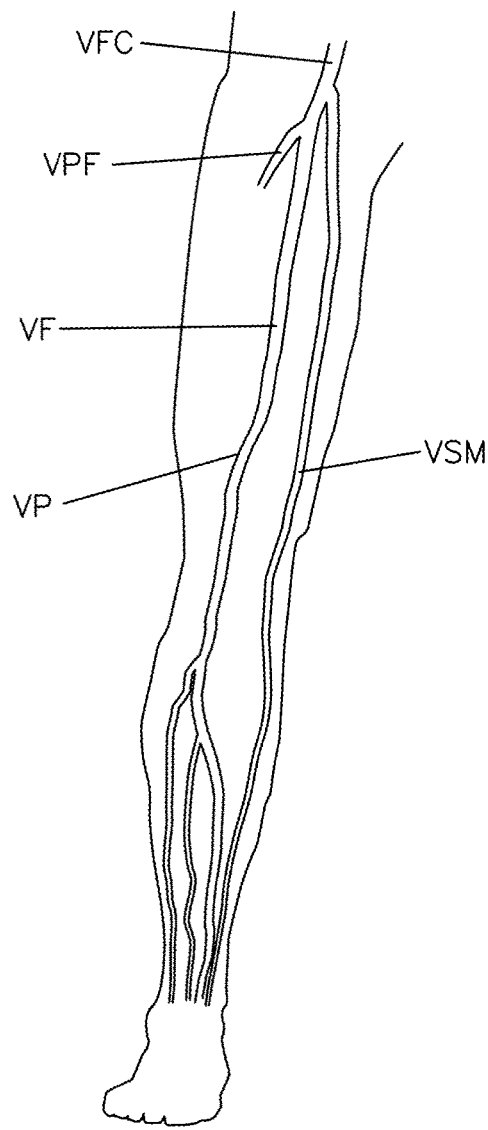
FIG. 24 schematically shows a leg with part of the venous system.

FIG. 24 shows several leg veins, namely vena poplitea VP, vena *femoralis* VF, vena *femoralis communis* VFC, vena *profunda* femoris VPF, and vena saphena *magna* VSM.

The catheter 41 with the balloon 45 and the covering 50 is introduced into the vena poplitea VP and thus into the deep leg venous system via a puncture in the hollow of the knee. The balloon 45 and the covering 50 are pushed up via the vena *femoralis* VF into the vena *femoralis communis* VPF and the covering is placed at the *magna* cross CM.

The devices described herein can be designed for single use and are provided in sterile form in packages.

From the preceding description, numerous modifications are accessible to a person skilled in the art without going beyond the scope of protection of the invention defined by the claims.

The cutter 20, 21 and/or the side openings 24 in the variant according to FIG. 17 can also be formed on a separately designed catheter which can be inserted into the vein after the covering 10, 50 has been placed and the device according to FIG. 1 or 20 has been removed.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A device for closing a vein juncture in the treatment of varicose veins, the device comprising:
    a catheter to be inserted into a venous system;
    an expandable balloon which is disposed at a distal end of the catheter, the expandable balloon being permanently attached to the catheter;
    a covering which is disposed circumferentially on the expandable balloon and configured to be expanded by said expandable balloon, the covering extending from a proximal covering end to a distal covering end, the proximal covering end being configured to be open, the covering being closed at the distal covering end, the covering on the expandable balloon having a maximum width of 0.5-1.5 cm in an expanded state, and an average thickness of at most 0.7 mm in a non-expanded state; and
    at least one adhesion agent configured to act on the covering when expanded such that the covering adheres to a vein wall in order to close the vein juncture,
    wherein the catheter includes:
        a first channel which fluidically connects a connection at a proximal end of the catheter to the expandable balloon, and
        a second channel which extends from an inlet opening at the proximal end of the catheter to an outlet opening at the distal end of the catheter and is configured to accommodate a guide wire.

2. The device according to claim 1, wherein the at least one adhesion agent is comprised by at least one of the following features:
    the covering is provided with an adhering outer layer,
    the covering comprises at least one reservoir with an adhesive,
    the covering has at least one hook configured to engage in the vein wall,
    at least one expandable lattice structure is provided to act on the covering such that the covering adheres to the vein wall,
    at least one adhesive channel is provided to guide the adhesive therethrough to apply the adhesive to the covering, and
    the at least one adhesion agent is configured to act between the covering and the vein wall.

3. The device according to claim 1, wherein the at least one adhesion agent is comprised by at least one of the following elements:
    the covering comprises at least one reservoir with a first adhesive, the at least one reservoir being configured to burst open when the covering is expanded and releases the adhesive,
    at least one expandable lattice structure is configured to act on the covering such that the covering adheres to the vein wall, the at least one expandable lattice structure being tubular,
    at least one expandable lattice structure is provided to act on the covering such that the covering adheres to the vein wall, the at least one expandable lattice structure being configured to be disposed at an effective distance from the distal covering end or from the proximal covering end or from both,
    at least two expandable lattice structures are disposed on the covering at an effective distance between the at least two expandable lattice structures, and
    at least one adhesive channel is provided through which a second adhesive is configured to be guided in order to be able to apply the second adhesive to the covering, the at least one adhesive channel being permanently connected to the catheter or being formed loosely from the catheter.

4. The device according to claim 1, wherein the covering has at least one of the following features:
    the distance between the proximal covering end and the distal covering end in a non-expanded state of the covering is less than 10 cm, and
    the covering is made of a biological or synthetic material.

5. The device according to claim 1, wherein the covering has at least one of the following features:
    the distance between the proximal covering end and the distal covering end in a non-expanded state of the covering is less than 8 cm, the distance between the proximal covering end and the distal covering end in a non-expanded state of the covering is in the range of 4-7 cm, and
    the covering is made of bovine pericardium.

6. The device according to claim 1, wherein the outlet opening is arranged radially offset with respect to the expandable balloon, so that the expandable balloon with the covering is configured be disposed laterally with respect to the guide wire then accommodated in the second channel, or wherein the outlet opening is axially offset with respect to the expandable balloon, so that the guide wire when accommodated in the second channel runs through the expandable balloon.

7. A device for closing a vein juncture in treatment of varicose veins, the device comprising:
    a catheter configured to be inserted into a venous system;
    an expandable balloon which is disposed at a distal end of the catheter, the expandable balloon being permanently attached to the catheter;
    a covering which is disposed circumferentially on the expandable balloon and configured to be expanded by said expandable balloon, the covering extending from a proximal covering end to a distal covering end, the proximal covering end being configured to be open, the covering being closed at the distal covering end, the covering on the expandable balloon having a maximum width of 0.5-1.5 cm in an expanded state, and an average thickness of at most 0.7 mm in a non-expanded state;
    at least one adhesion agent configured to act on the covering when expanded such that the covering adheres to a vein wall in order to close the vein juncture; and
    a guide wire onto which the catheter is configured to be pushed.

8. A device for closing a vein juncture in treatment of varicose veins, the device comprising:
    a catheter configured to be inserted into a venous system;
    a balloon which is expandable and which is disposed at a distal end of the catheter;
    a covering which is disposed circumferentially on the balloon and configured to be expanded by said balloon, the covering extending from a proximal covering end to a distal covering end, the proximal covering end being configured to be open, and the distal covering end being designed to be closed;

at least one adhesion agent configured to act on the covering when expanded such that the covering adheres to a vein wall in order to close the vein juncture;

a first channel which fluidically connects a connection at the proximal end of the catheter to the balloon; and a second channel which extends from an inlet opening at the proximal end of the catheter to an outlet opening at the distal end of the catheter and is configured to accommodate a guide wire, wherein the outlet opening is arranged radially offset with respect to the balloon, so that the balloon with the covering is configured to be disposed laterally with respect to the guide wire when accommodated in the second channel, and the first channel and the second channel are attached to the catheter.

9. The device according to claim 8, further comprising a cutter configured to cut at least part of an inner wall of a vein leading to the vein juncture.

10. The device according to claim 9, wherein the cutter is disposed on the catheter or on another catheter formed separately therefrom.

11. The device according to claim 9, wherein the cutter includes a cutting balloon which is expandable and includes at least one cutting element.

12. The device according to claim 8, further comprising a feed channel with side openings through which a sclerosant is configured to be introduced into a vein of the varicose veins.

13. The device according to claim 12, wherein the catheter or another catheter formed separately therefrom includes the feed channel with the side openings.

14. The device according to claim 8, further comprising an inner catheter configured to treat a vein, of the varicose veins, leading to the vein juncture, the inner catheter being configured to be inserted into the catheter or another catheter and into which a sclerosant is configured to be introduced, the inner catheter having side openings.

15. The device according to claim 14, wherein the inner catheter is configured to be closed at a distal end thereof.

16. The device according to claim 14, wherein the inner catheter includes a plurality of side openings.

17. The device according to claim 8, wherein the proximal covering end remains open when the covering adheres to the vein wall.

18. A device for closing a vein juncture in the treatment of varicose veins and for treating a vein leading to the vein juncture, the device comprising:

a catheter configured to be inserted into a venous system;

a first balloon which is expandable and which is disposed at a distal end of the catheter;

a covering which is disposed circumferentially on the first balloon and is configured to be expanded by said first balloon, the covering extending from a proximal covering end to a distal covering end, and the proximal covering end being configured to be open;

at least one adhesion agent configured to act on the covering when expanded such that the covering adheres to a vein wall in order to close the vein juncture;

a feed channel with side openings through which a sclerosant is configured to be introduced into the vein; and a cutter configured to cut intima and media of the vein, the cutter extending along the longitudinal axis of the device, the cutter including a second balloon which is expandable and configured to cut, the side openings of the feed channel being disposed closer to a proximal end of the catheter than the second balloon.

19. The device according to claim 18, wherein the cutter is parallel to the balloon.

* * * * *